US012636267B2

(12) United States Patent (10) Patent No.: US 12,636,267 B2

Lee et al. (45) Date of Patent: May 26, 2026

(54) NICLOSAMIDE DELAYED-RELEASE COMPOSITION AND ANTIVIRAL USE THEREOF

(71) Applicants: DAEWOONG THERAPEUTICS INC., Suwon-si (KR); DAEWOONG PHARMACEUTICAL CO., LTD., Hwaseong-si (KR)

(72) Inventors: Minsuk Lee, Seoul (KR); Bokki Kang, Seongnam-si (KR); Sanghan Park, Seoul (KR); Donghwan Kim, Suwon-si (KR)

(73) Assignees: DAEWOONG THERAPEUTICS INC., Suwon-si (KR); DAEWOONG PHARMACEUTICAL CO., LTD., Hwaseong-si (KR)

( * ) Notice: Subject to any disclaimer, the term of this patent is extended or adjusted under 35 U.S.C. 154(b) by 1054 days.

(21) Appl. No.: 17/637,178

(22) PCT Filed: Aug. 21, 2020

(86) PCT No.: PCT/KR2020/011196

§ 371 (c)(1),
(2) Date: Jun. 30, 2022

(87) PCT Pub. No.: WO2021/040337

PCT Pub. Date: Mar. 4, 2021

(65) Prior Publication Data

US 2023/0000803 A1 Jan. 5, 2023

(30) Foreign Application Priority Data

| Aug. 23, 2019 | (KR) | ........................ | 10-2019-0103824 |
| Mar. 27, 2020 | (KR) | ........................ | 10-2020-0037560 |
| Apr. 10, 2020 | (KR) | ........................ | 10-2020-0044237 |
| Aug. 12, 2020 | (KR) | ........................ | 10-2020-0101136 |

(51) Int. Cl.
*A61K 31/167* (2006.01)
*A61P 31/12* (2006.01)

(52) U.S. Cl.
CPC ............ *A61K 31/167* (2013.01); *A61P 31/12* (2018.01)

(58) Field of Classification Search
CPC .. A61K 31/167; A61K 31/609; A61K 9/0019; A61K 47/02; A61K 47/26; A61K 47/38; A61P 31/12; A61P 31/14
See application file for complete search history.

(56) References Cited

U.S. PATENT DOCUMENTS

| 7,544,712 | B1 | 6/2009 | Hsu et al. |
| 2009/0149545 | A1 | 6/2009 | Hsu et al. |
| 2015/0065526 | A1 | 3/2015 | Deng et al. |

FOREIGN PATENT DOCUMENTS

| CN | 101007170 A | 8/2007 | |
| CN | 101317564 A | 12/2008 | |
| CN | 107811967 A | 3/2018 | |
| CN | 108935457 A | 12/2018 | |
| JP | 2007-509148 A | 4/2007 | |
| RU | 2 617 049 C1 | 4/2017 | |
| WO | WO-2016077787 A1 * | 5/2016 | ........... A61K 31/661 |
| WO | WO-2017223491 A1 * | 12/2017 | ........... A61K 31/167 |

OTHER PUBLICATIONS

"Fabrication of Niclosamide loaded solid lipid nanoparticles: in vitro characterization and comparative in vivo evaluation." Rehman, M. U., Khan, M. A., Khan, W. S., Shafique, M., & Khan, M. (2017). Artificial Cells, Nanomedicine, and Biotechnology, 46(8), 1926-1934. (Year: 2017).*

"Preclinical evaluation of a nanoformulated antihelminthic, niclosamide, in ovarian cancer" Lin et al. Oncotarget, vol. 7, pp. 8993-9006 (Year: 2016).*

Extended European Search Report issued Jan. 30, 2023 in European Application No. 20857855.9.

Chang-Jer Wu et al., "Inhibition of Severe Acute Respiratory Syndrome Coronavirus Replication by Niclosamide", Antimicrobial Agents and Chemotherapy, Jul. 2004, pp. 2693-2696, vol. 48, No. 7.

International Search Report of PCT/KR2020/011196 dated Nov. 26, 2020 [PCT/ISA/210].

Office Action dated Mar. 31, 2022 from the Intellectual Property Office of India in IN Application No. 202247014810.

Office Action dated Jun. 23, 2022 from the Korean Intellectual Property Office in KR Application No. 10-2020-0101136.

Vietnamese Office Action dated Nov. 27, 2025, issued in Vietnamese application No. 1-2022-01282.

* cited by examiner

*Primary Examiner* — Kara R. Mcmillian
*Assistant Examiner* — Sophia P Hirakis
(74) *Attorney, Agent, or Firm* — Sughrue Mion, PLLC

(57) ABSTRACT

The present invention relates to a pharmaceutical composition for prevention or treatment of coronavirus infections, comprising a delayed-release composition of niclosamide or a pharmaceutically acceptable salt thereof, and a method for preventing or treating coronavirus infections by using the same.

1 Claim, 7 Drawing Sheets

Specification includes a Sequence Listing.

[Fig. 1]
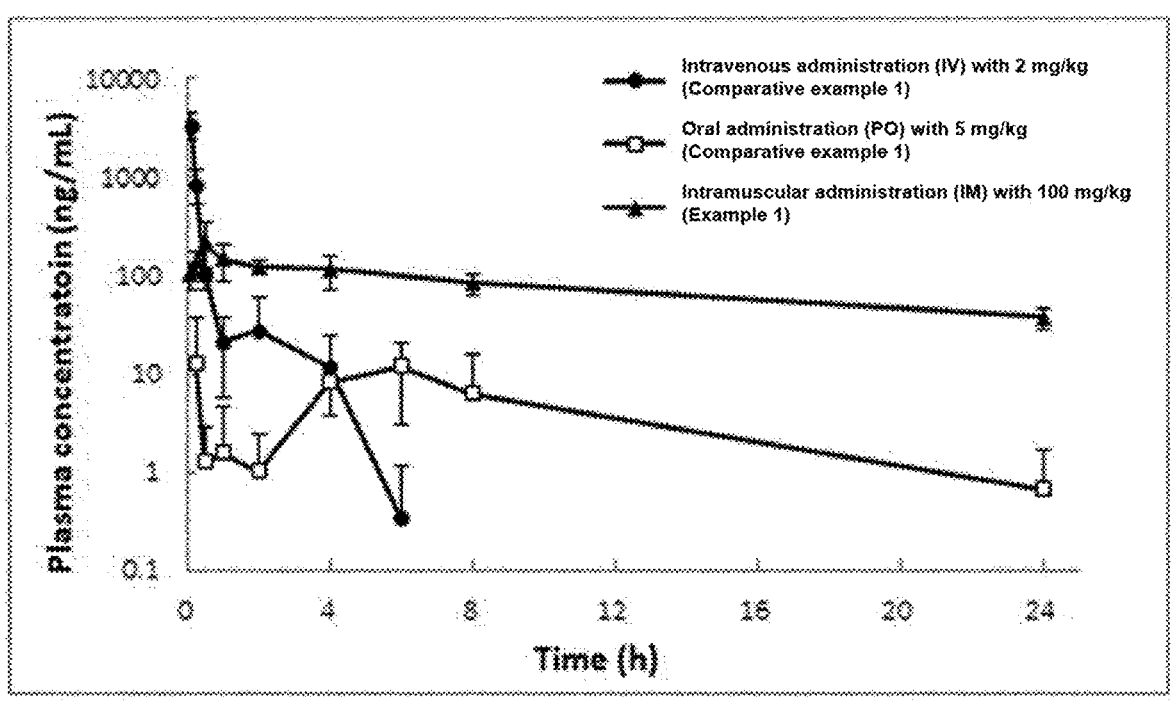

[Fig. 2]
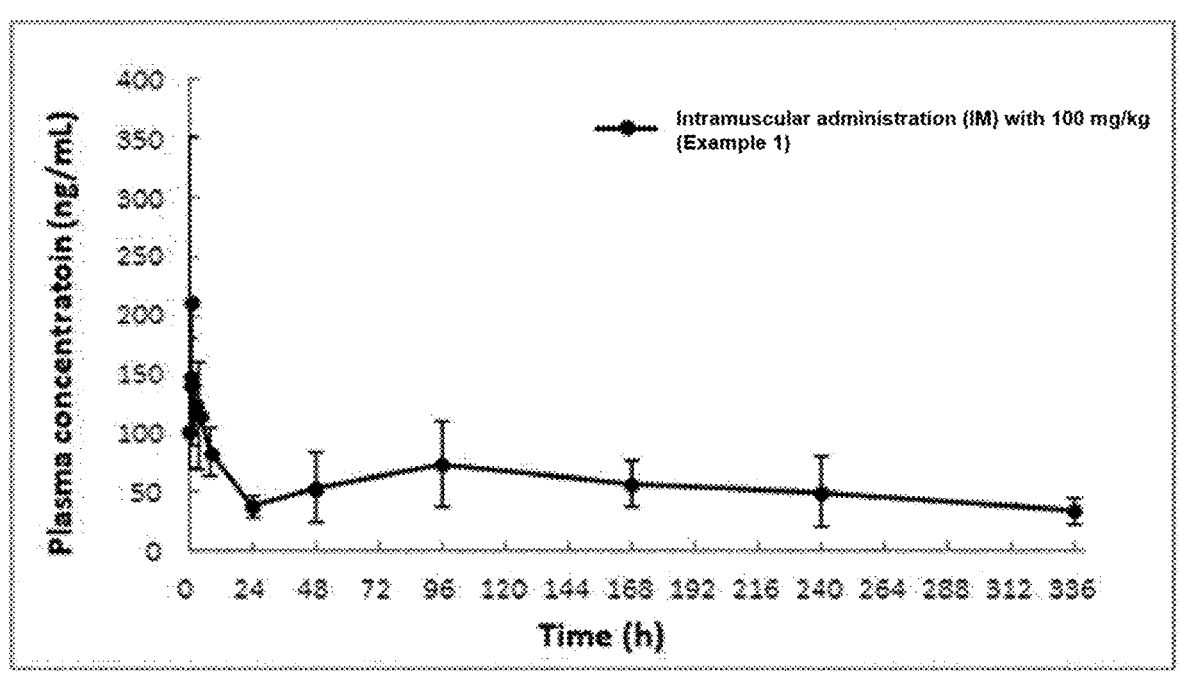

[Fig. 3]
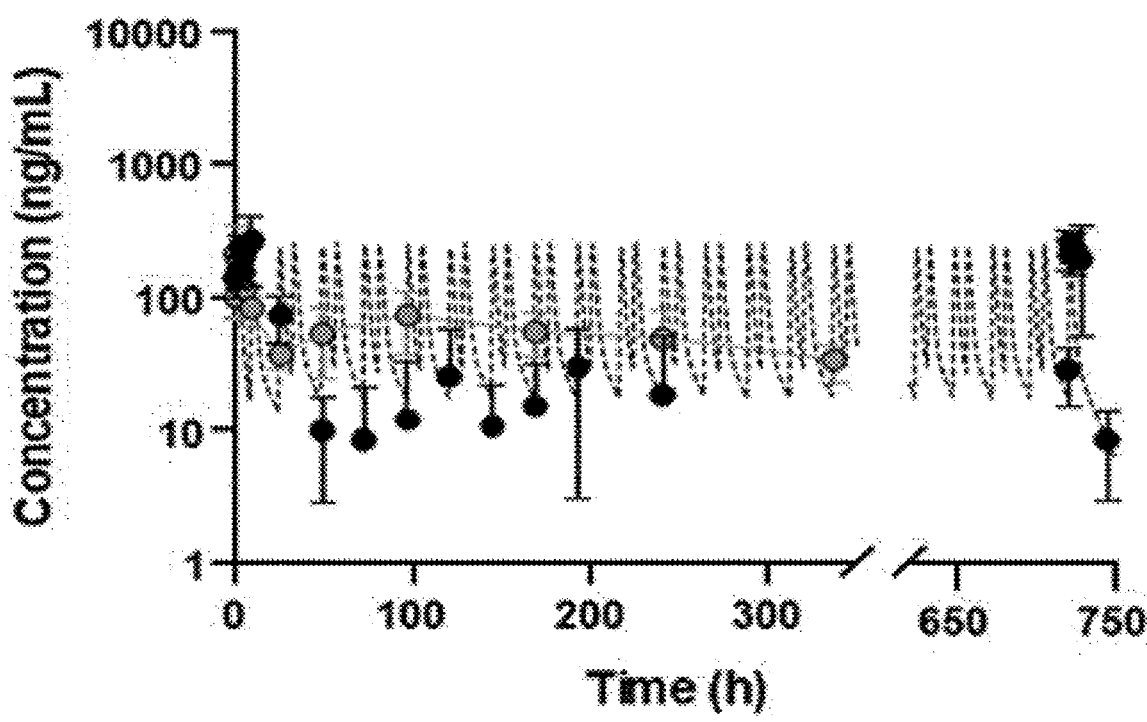
Oral administration (PO)_ simulation with 150mg/kg twice a day (300 mg/kg/day)
(Comparative example 1)
Oral administration (PO)_observed with 150mg/kg twice a day (300 mg/kg/day)
(Comparative example 2)
Intramuscular administration (IM)_observed with 100mg/kg once (100 mg/kg/day)
(Example 1)

[Fig. 4]
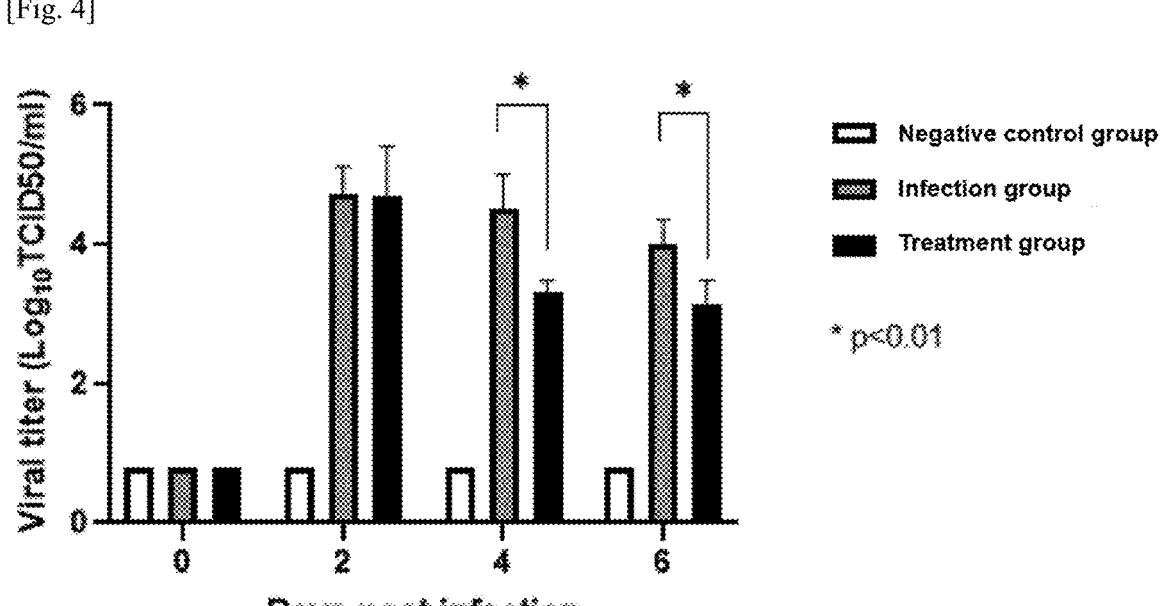

[Fig. 5]
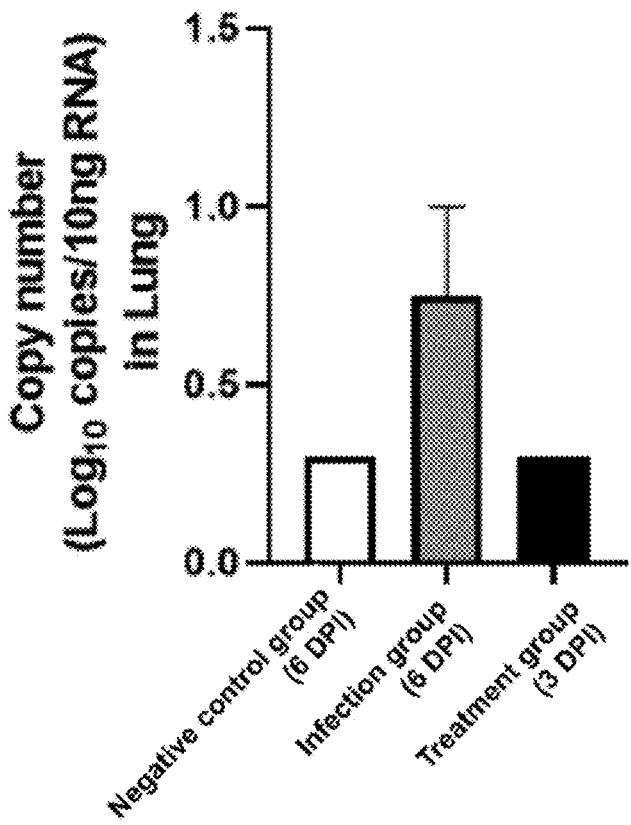

[Fig. 6]
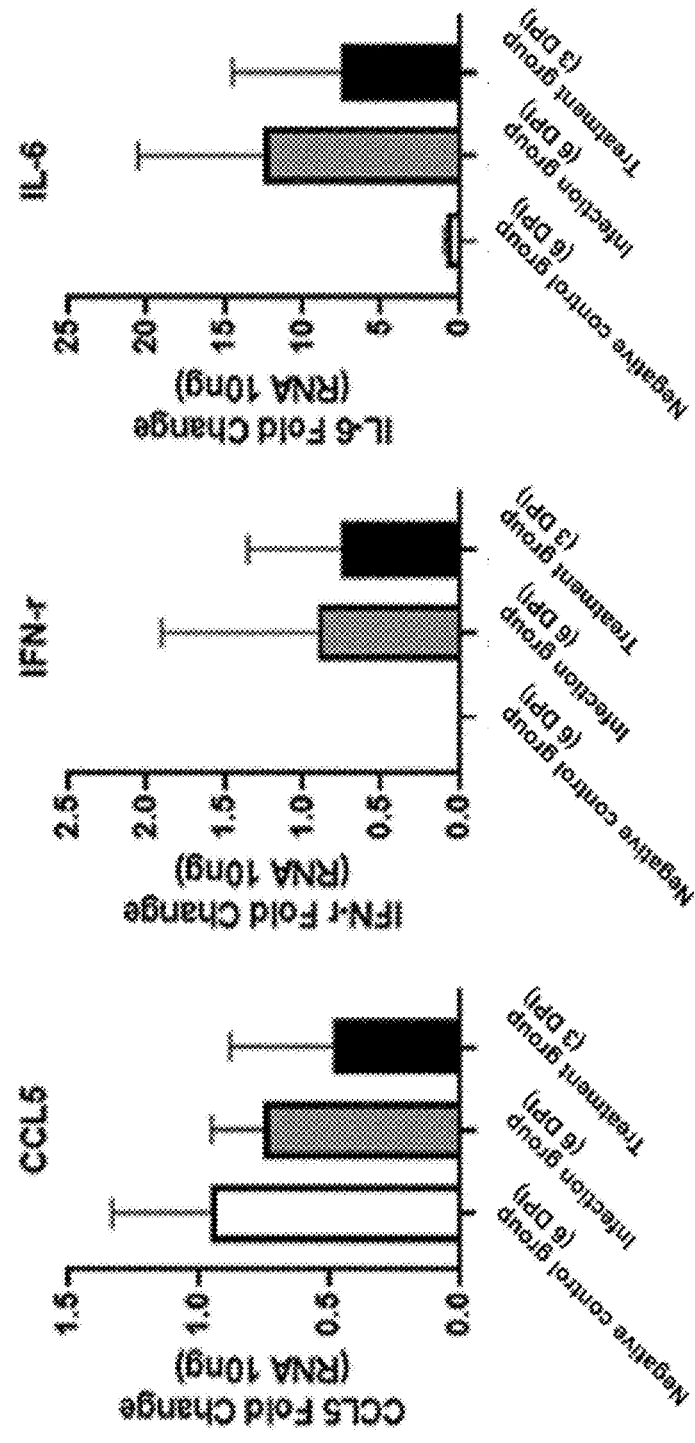

[Fig. 7]
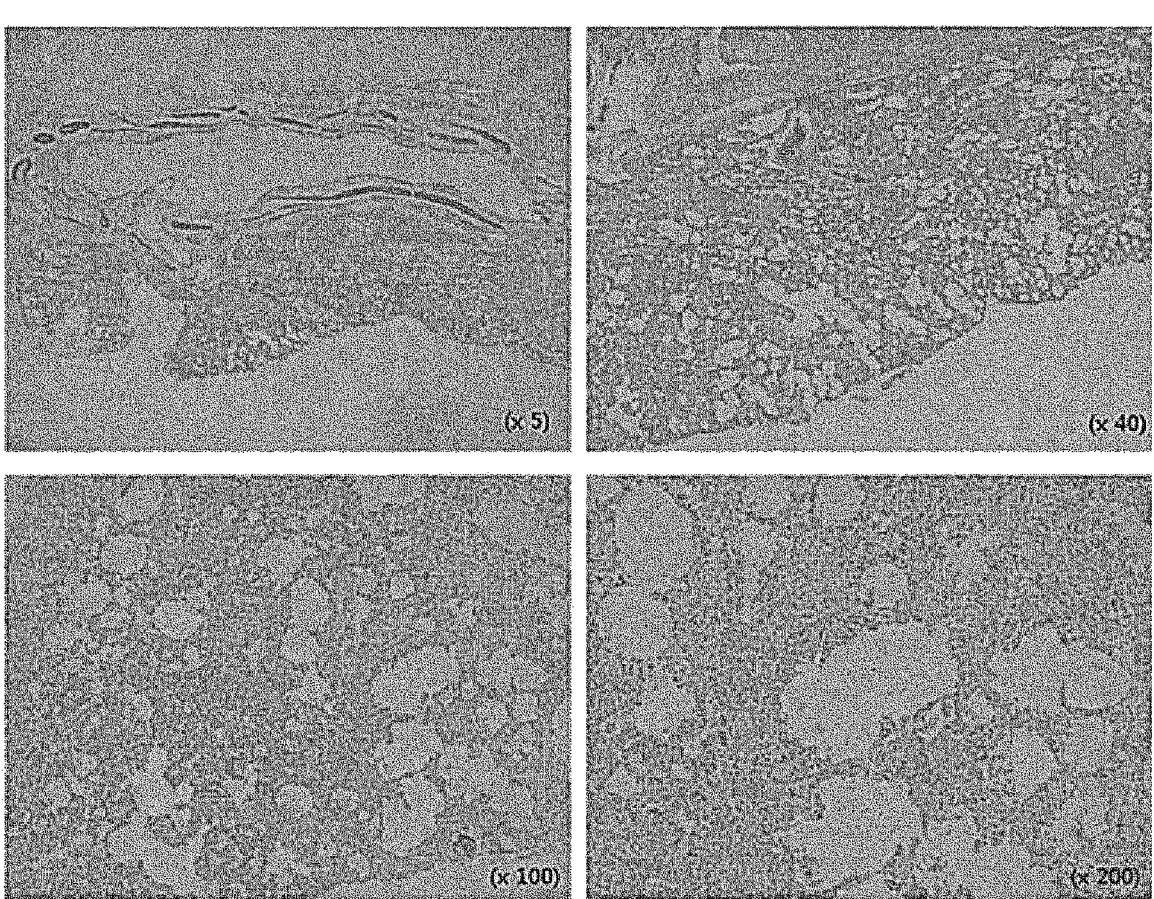

NICLOSAMIDE DELAYED-RELEASE COMPOSITION AND ANTIVIRAL USE THEREOF

CROSS REFERENCE TO RELATED APPLICATIONS

This application is a National Stage of International Application No. PCT/KR2020/011196 filed Aug. 21, 2020, claiming priority based on Korean Patent Application No. 10-2019-0103824 filed Aug. 23, 2019, Korean Patent Application No. 10-2020-0037560 filed Mar. 27, 2020, Korean Patent Application No. 10-2020-0044237 filed Apr. 10, 2020, and Korean Patent Application No. 10-2020-0101136 filed Aug. 12, 2020, the entire disclosures of which are incorporated herein by reference.

INCORPORATION BY REFERENCE

The content of the electronically submitted sequence listing, file name: Q272309_Sequence_Listing.txt; size: 2443 bytes; and date of creation: Feb. 16, 2022, filed herewith, is incorporated herein by reference in its entirety.

TECHNICAL FIELD

The present invention relates to a pharmaceutical composition for prevention or treatment of coronavirus infections, comprising a delayed-release composition of niclosamide or a pharmaceutically acceptable salt thereof, and a method for preventing or treating coronavirus infections by using the same.

BACKGROUND ART

The emergence of coronavirus (CoV), which causes Severe Acute Respiratory Syndrome (SARS) and Middle East Respiratory Syndrome (MERS), poses a severe threat to public health.

Coronaviruses are known to mainly cause pneumonia and enteritis in humans and animals, and are also known to occasionally cause nervous system infections and hepatitis. Coronaviruses belong to the family Coronaviridae and are positive sense RNA viruses with a spherical outer membrane of about 100-120 nm in size. Coronaviruses consist of a total of five structural proteins, including the outermost spike protein (S), hemagglutinin-esterase (HE) protein, transmembrane (M) protein, small membrane (E) protein, and nucleocapsid (N) protein (Lai and Homes, 2001. Fields Virology). Among the above, the spike protein acts as a ligand binding to a cell receptor and induces fusion between the host cell and the virus, and is known as the most mutable protein.

Both SARS and MERS are known to be caused by variant coronaviruses (SARS-CoV and MERS-CoV) which belong to the genus Beta coronavirus. Accordingly, SARS-CoV and MERS-CoV share similar characteristics in clinical symptoms, etiology and infection. In the phylogenetic tree, SARS-CoV belongs to lineage B, which contains bat SARS-like coronaviruses and other bat-derived CoVs, and MERS-CoV belongs to lineage C, which contains bat-derived CoVs.

Since coronaviruses are highly mutated, using a current antiviral agent again has the drawback of having a low effect if the antiviral drug does not match the most recent virus type. Accordingly, there is a continuous demand for the development of an antiviral agent with excellent anti-infection and therapeutic effects.

DESCRIPTION OF EMBODIMENTS

Technical Problem

The technical problem to be solved by the present invention is to provide a pharmaceutical composition for prevention or treatment of coronavirus infections, comprising a delayed-release composition of niclosamide or a pharmaceutically acceptable salt thereof.

Also, the technical problem to be solved by the present invention is to provide a method for preventing or treating coronavirus infections by using the delayed-release composition.

Technical Solution

According to an aspect of the present invention relates to a pharmaceutical composition for prevention or treatment of coronavirus infections, comprising a delayed-release composition of niclosamide or a pharmaceutically acceptable salt thereof.

As used herein, "niclosamide" is an oral salicyl anilide derivative which was approved by the FDA in 1960 and used for the treatment of various parasitic infections for nearly 50 years. These conventional niclosamide formulations had very low water solubility and intestinal permeability, and bioavailability was extremely low, it was impossible to achieve and maintain a blood drug concentration to achieve antiviral activity in the body. In particular, the clearance of the drug was found to be extremely fast during oral administration, there was a problem in that the existing formulation made it impossible to administer niclosamide to the body for antiviral purposes.

The delayed-release composition of the present invention solves the problems of the conventional niclosamide formulations described above and presents PK profile characteristics capable of exhibiting antiviral activity, thereby presenting effective antiviral activity by maintaining an effective blood drug concentration for a long time.

In one embodiment, the delayed-release composition may comprise niclosamide or a pharmaceutically acceptable salt thereof and an anionic polysaccharide cellulose derivative.

In one embodiment, the anionic polysaccharide may be a carboxy polysaccharide, and the anionic polysaccharide cellulose derivative may be carboxymethyl cellulose, carboxyethyl cellulose, carboxymethyl chitosan or carboxymethyl dextran, but is not limited thereto.

In one embodiment, the anionic polysaccharide cellulose derivative may be carboxymethyl cellulose, but any polymer applied as an excipient of the pharmaceutical formulation exhibiting the effect of the present application may be used as the anionic polysaccharide cellulose derivative without limitation.

In one embodiment, the composition may further comprise a phosphate salt and sodium salt. The phosphate salt and sodium salt may be derived from sodium phosphate monobasic monohydrate, but is not limited thereto.

In one embodiment, the delayed-release composition may further comprise mannitol, but is not limited thereto, and any excipient that is applicable to an injection formulation as a sugar alcohol may be changed as needed and used.

In an exemplary embodiment of the present invention, a niclosamide delayed-release composition comprising an anionic polysaccharide cellulose derivative was prepared, and it was confirmed that a target blood drug concentration may be achieved and maintained in the prepared composition (FIG. 1 and Table 2), and an effective antiviral effect may be exhibited (FIGS. 2 to 4).

In one embodiment, the pharmaceutical composition of the present invention may be a parenteral administration formulation, and specifically, the parenteral administration may be performed subcutaneously or intramuscularly.

In addition, the pharmaceutical composition of the present invention may be applied in a pharmaceutically effective amount, and "pharmaceutically effective amount" means an amount sufficient to treat a disease with a reasonable benefit/risk ratio applicable to medical treatment. The effective dosage level may be determined according to factors including patient's gender, age, type of disease, severity, drug activity, drug sensitivity, administration time, administration route and excretion rate, duration of treatment, concomitant drugs, and other factors well known in the medical field.

Another aspect of the present invention relates to a method for preventing or treating coronavirus infections, comprising administering to an individual a delayed-release composition of niclosamide or a pharmaceutically acceptable salt thereof.

The term "individual" as used herein includes animals or humans with coronavirus infection whose symptoms may be improved by administering the pharmaceutical composition according to the present invention. Coronavirus infection may be prevented and treated effectively by administering to an individual the composition for treatment according to the present invention.

In one embodiment, the delayed-release composition may comprise niclosamide or a pharmaceutically acceptable salt thereof and an anionic polysaccharide cellulose derivative.

In one embodiment, the anionic polysaccharide may be a carboxy polysaccharide, and the anionic polysaccharide cellulose derivative may be carboxymethyl cellulose, carboxyethyl cellulose, carboxymethyl chitosan or carboxymethyl dextran, but is not limited thereto.

In one embodiment, the anionic polysaccharide cellulose derivative may be carboxymethyl cellulose.

The term "administration" as used herein means introducing a predetermined substance into humans or animals by any suitable method. As to the administration route of the composition for treatment according to the present invention, the composition for treatment may be administered orally or parenterally through any general route as long as it can reach a target tissue. Also, the composition for treatment according to the present invention may be administered by any device capable of moving an active ingredient to a target cell. Specifically, the administration may be parenteral administration.

The preferred dosage of the pharmaceutical composition according to the present invention varies depending on the condition and weight of the patient, the severity of disease, the drug form, the route and duration of administration, but may be properly selected by a person skilled in the art.

Advantageous Effects of Invention

The pharmaceutical composition for prevention or treatment of coronavirus infections, comprising a delayed-release composition of niclosamide or a pharmaceutically acceptable salt thereof according to the present invention overcomes the drawbacks of conventional niclosamide formulations by allowing for the long-term maintenance of effective drug concentrations in blood and a target organ, resulting in effective antiviral activity and an effect for preventing or treating coronavirus infection.

The formulation of the present invention allows for the long-term maintenance of an effective blood drug concentration of a poorly soluble drug, allowing the formulation to be used for all diseases in which niclosamide has therapeutic effects, such as viral infections other than coronavirus, intractable lung diseases, and so on, thereby significantly increasing the therapeutic effect.

BRIEF DESCRIPTION OF THE DRAWINGS

FIG. 1 shows the result of measuring plasma concentration for 24 hours after administering the formulations of Comparative example 1 and Example 1.

FIG. 2 shows the result of measuring plasma concentration for 336 hours after administering the formulation of Example 1.

FIG. 3 shows the result of measuring plasma concentration for 750 hours after administering the formulations of Comparative example 1, Comparative example 2, and Example 1.

FIG. 4 shows the result of confirming a significant viral titer reduction effect in the nasal wash sample when Example 1 is administered after SARS-CoV-2 virus infection.

FIG. 5 shows the result of viral titer reduction in a lung tissue when Example 1 is administered after SARS-CoV-2 virus infection.

FIG. 6 shows the result of reduction of CCL5, IFN-$\gamma$ and IL-6 which induce cytokine storm and inflammatory cell infiltration into lung tissue when Example 1 is administered after SARS-CoV-2 virus infection.

FIG. 7 shows the result confirming that the inflammation in the lung tissue is treated when Example 1 is administered after SARS-CoV-2 virus infection.

DETAILED DESCRIPTION OF EXEMPLARY EMBODIMENTS

Hereinafter, the present invention will be described by means of the examples. However, the following examples only exemplify the present invention, and are not intended to limit the present invention.

Example 1. Preparation of Niclosamide Delayed-Release Composition

A niclosamide formulation was prepared according to the composition of the following table 1. Sodium carboxymethylcellulose, sodium phosphate monobasic monohydrate, and mannitol were added to water for injection, stirred and completely dissolved, and then niclosamide was added and stirred. After homogenizing the mixture with a homomixer, the sterilizing step was carried out by autoclaving at 121° C. for 15 minutes. Thereafter, the drug particle size was adjusted to a desired particle size using wet milling, and performing post-sterilization as needed.

TABLE 1

| Component | Function | Content (%, w/w) |
| --- | --- | --- |
| niclosamide | active ingredient | 21.87 |
| sodium carboxymethylcellulose | suspending agent | 0.80 |
| sodium phosphate monobasic monohydrate | buffer solution | 0.07 |
| mannitol | suspending agent | 4.37 |
| water | water for injection | 72.89 |
| Total | | 100 |

Comparative Example 1. Niclosamide Comparative
Formulation 1

The efficacy of conventional niclosamide was tested in vitro in a form dissolved in DMSO due to its poor solubility, and comparative formulation 1 was prepared with reference to such an existing formulation.

Following the addition of an appropriate amount of niclosamide, DMSO corresponding to 10% of the total volume was added, followed by PEG400 corresponding to 30% of the entire volume. Thereafter, the pH was adjusted to 6~7 by adding 0.05 N of NaOH corresponding to 20% of the total volume, and then the mixture was completely dissolved by sonication.

Finally, saline corresponding to 40% of the remaining total volume was added to prepare niclosamide in a concentration of 2~5 mg/mL.

Comparative Example 2. Niclosamide Comparative
Formulation 2

A vehicle solution was prepared by mixing purified water to contain 0.2% (v/v) Tween 80 and 0.5% (w/v) sodium carboxymethylcellulose based on the total volume.

Thereafter, niclosamide was weighed and added to the vehicle solution until the final niclosamide content was 30 mg/mL, and the mixture was dispersed by vortexing to prepare comparative formulation 2.

Experimental Example 1. Comparison 1 of PK
Profiles Between the Conventional Niclosamide
Formulation and the Composition of the Present
Invention Male white SD rats (7 weeks old, Orient Bio Inc., Seongnam, Korea) weighing 187.5-224.0 g were used. White rats were fasted for 14 hours before the experiment, and the fasting was maintained until 4 hours after administration. The kennel provided light and shade for 12 hours and maintained the appropriate temperature (20~25° C.) and humidity (40~60%).

The formulations in Example 1 and Comparative example 1 were administered to the animal model according to the following table 2.

TABLE 2

| No. | Administered substance | Administration route | Number of animals | Dosage |
|---|---|---|---|---|
| 1 | Comparative example 1 | intravenous administration (IV) | 6 | 2 mg/kg |
| 2 | Comparative example 1 | oral administration (PO) | 5 | 5 mg/kg |
| 3 | Example 1 | intramuscular administration (IM) | 6 | 100 mg/kg |

After administering the drug as described above, pharmacokinetic tests were performed on the formulation of Comparative example 1 and the formulation of Example 1 of the present invention.

Specifically, niclosamide was intravenously administered to the fasted white rats at a dose of 2 mg/kg through the caudal vein or orally administered at a dose of 5 mg/kg using an oral needle. In the case of intramuscular injection, niclosamide was injected into the right thigh muscle at a dose of 100 mg/kg using a 26 G needle. 5 minutes (for the intravenously administered group only), 15 minutes, 30 minutes, 1 hour, 2 hours, 4 hours, 6 hours, 8 hours and 24 hours after intravenous and oral administration, and 5 minutes, 15 minutes, 30 minutes, 1 hour, 2 hours, 4 hours, 8 hours, 24 hours, 48 hours, 96 hours, 168 hours, 240 hours and 336 hours after intramuscular injection, the white rats were immobilized in a frame, and 150 μL of blood was collected from the jugular vein using a 1 mL syringe coated with heparin. After centrifuging the blood collected for 5 minutes, plasma was separated and frozen at −20° C. until analysis.

The concentration of niclosamide in the plasma sample was quantified using an HPLC/MS/MS system. The pretreatment process of the sample is as follows. For standard samples for calibration curves, niclosamide was serially diluted with acetonitrile to prepare a standard material (1, 2, 3, 10, 30, 100, 300, 1,000, 2,000, 3,000 and 5,000 ng/mL), and then 20 μL of empty plasma, 20 μL of internal standard solution (ibuprofen 1 μg/mL in acetonitrile) and 140 μL of acetonitrile were added to 20 μL of the standard material for pretreatment. For quality control samples, standard materials for quality control samples (5, 500, 4,500 ng/mL) were prepared, and then pre-treated in the same way as standard samples for calibration curves. For plasma samples, protein precipitation was induced by adding 20 μL of internal standard solution and 160 μL of acetonitrile to a sample of 20 μL. Then, the mixed sample was suspended for 10 minutes using a vortex mixer and centrifuged at 13,500 rpm for 10 minutes, so that 150 μL of the supernatant was taken and transferred to an analysis vessel, and 5 μL of the same was injected into the HPLC/MS/MS system, to be analyzed.

HPLC/MS/MS analysis conditions are as follows.

HPLC System: Agilent 1100 (Agilent Technologies, Santa Clara, CA)

Column: ZORBAX® Phenyl 5 μm, 2.1*50 mm (Agilent)

Mobile phase:

A: 10 mM Ammonium formate

B: Acetonitrile

[Isocratic Elution]

| Time | 0 → 3.0 |
|---|---|
| B (%) | 70 → 70 |

Flow rate: 300 μL/min

Temperature: column 40° C. and autosampler tray 10° C.

Run time: 3 minutes

Detection: Tandem quadrupole mass spectrometer (API 4000, QTRAP®, Applied Biosystems/MDS SCIEX, Foster City, CA, USA)

curtain gas: 20 psi ion source gas 1: 50 psi ion source gas 2: 50 psi ionspray voltage: −4200 V temperature: 600° C.

multiple-reaction-monitoring (MRM) mode: negative

Molecule ions of niclosamide and ibuprofen were fragmented by collision energy of −38 V and −10 V, respectively, and the collision gas was set to 'medium (8 psi)' in the equipment. Ion detection was performed in ESI negative MRM mode, and the two channels were simultaneously quantified, niclosamide at m/z 324.92→170.90, and ibuprofen at m/z 205.06→161.10. Integration of the detection peak was performed using Analyst software version 1.6.2 (Applied Biosystems/MDS SCIEX).

The quantitation range of niclosamide in plasma was 0.001~5.0 μg/mL, and in the corresponding analysis, niclosamide showed a peak retention time of 0.80 minutes and ibuprofen showed a peak retention time of 0.76 minutes.

The concentration of niclosamide in plasma over time was obtained using the LC-MS/MS method described above, and the pharmacokinetic parameters were calculated by non-compartmental analysis of WinNonlin® 4.2 (Pharsight Corp., Cary, NC, USA) software.

The maximum plasma concentration ($C_{max}$) and the time to reach maximum concentration ($T_{max}$) were obtained over time from a curve according to blood drug concentration versus time, and the elimination rate constant ($K_e$) was calculated using linear regression analysis in the log scale terminal phase. The half-life ($T_{1/2}$) was obtained by dividing LN2 by $K_e$, and the area under blood drug concentration versus time curve ($AUC_{0-\infty}$) and the area under blood drug moment versus time curve ($AUMC_{0-\infty}$) were calculated by the linear trapezoidal rule and the standard area extrapolation method. The clearance (CL) and the steady state volume of distribution ($V_{ss}$) were calculated by the following equations (1~3).

$$CL = \frac{Dose}{AUC_{0-\infty}} \quad \text{(Equation 1)}$$

$$V_{ss} = MRT \times CL \quad \text{(Equation 2)}$$

$$MRT = \frac{AUMC_{0-\infty}}{AUC_{0-\infty}} \quad \text{(Equation 3)}$$

The PK profile of the conventional niclosamide formulation (Comparative example 1) and the formulation in Example 1 of the present invention was compared using the above method.

As a result, when Example 1 was administered, it was confirmed that the blood drug concentration was maintained remarkably higher than when Comparative example 1 was administered (FIG. 1). In addition, when Comparative example 1 was intravenously administered, the blood drug concentration was reduced to 1 ng/mL or less within 8 hours, and even when Comparative example 1 was orally administered, the blood drug concentration was reduced to 1 ng/mL or less after 24 hours.

It was also confirmed whether the blood drug concentration was maintained for a long time after Example 1 was administered. As a result, as shown in FIG. 2, it was confirmed that the blood drug concentration could be maintained up to 336 hours when Example 1 was administered.

Furthermore, as shown in the following table 3, when Comparative example 1 was intravenously administered, the dosage was limited due to the solubility limitations, and the half-life was 1 hour, resulting in very rapid clearance, and when Comparative example 1 was orally administered, $C_{max}$ was at a level of 21 ng/ml, it was found that it was impossible to achieve the required in vivo exposure for activity.

On the other hand, in the case of the formulation in Example 1 of the present invention, $C_{max}$ was at a level of 223 ng/ml and a half-life of 9 days or longer, and thus it was confirmed that the in vivo exposure required for antiviral activity could be sufficiently achieved.

TABLE 3

| | Comparative example 1 intravenously administered | Comparative example 1 orally administered | Example 1 |
|---|---|---|---|
| $T_{max}$ (h) | 0.08 ± 0.000 | 4.05 ± 2.35 | 0.83 ± 0.61 |
| $C_{max}$ (ng/mL) | 3,496 ± 1,109 | 20.7 ± 20.4 | 223 ± 129 |
| $T_{1/2}$ (h) | 1.08 ± 0.83 | 5.26 ± 4.97 | 227 ± 102 |
| $AUC_{last}$ (ng · h/mL) | 1,044 ± 328 | 77.4 ± 46.3 | 18,518 ± 4,500 |
| $AUC_{inf}$ (ng · h/mL) | 1,053 ± 332 | 79.3 ± 55.5 | 29,824 ± 6,306 |
| CL (mL/h/kg) | 2,107 ± 835 | — | — |
| $V_{ss}$ (mL/kg) | 600 ± 207 | — | — |
| F (%) | — | 2.97 ± 1.77 | 35.5 ± 8.6 |

As described above, even when niclosamide was completely dissolved and orally administered, the bioavailability was found to be exceedingly poor, making it unable to obtain and maintain the target blood drug concentration. When niclosamide is orally administered, a strong reduction occurred by the microorganisms in the intestines and glucuronidation of the drug itself occurred in the intestines, thus, when orally administered, even when the drug is excessively administered or administered in a form completely dissolved, the desired systemic action of the drug cannot be achieved because a strong first-pass effect occurs in the intestines.

Experimental Example 2. Comparison 2 of PK Profiles Between the Conventional Niclosamide Formulation and the Composition of the Present Invention The PK profile was compared after increasing the dose of the orally administered formulation in Comparative example 2 using the same method as in Experimental example 1.

Specifically, in order to overcome the very short half-life of the drug, Comparative example 2 was administered at a dose of 150 mg/kg twice a day (morning, evening, 8 hours apart). Blood was drawn and the blood drug concentration was measured at 0 hour, 0.5 hour, 1 hour, 2 hours, 4 hours, 8 hours, 24 hours (1 day), 2 days, 3 days, 4 days, 5 days, 6 days, 7 days, 8 days, 10 days, 15 days, 20 days, 25 days, 30 days after the first administration (Day 1), and 0.5 hour, 1 hour, 4 hours, 8 hours, and 24 hours after the last administration (Day 30). The measured data was compared with the data of Example 1 in Experimental example 1.

TABLE 4

| No. | Administered substance | Administration route | Number of animals | Dosage |
|---|---|---|---|---|
| 1 | Comparative example 2 | oral administration (PO) | 8 | 300 mg/kg/day |
| 2 | Example 1 | intramuscular administration (IM) | 6 | 100 mg/kg single dose |

As a result, when Comparative example 2 was orally administered repeatedly at a dose of 150 mg/kg twice a day, the maximum plasma concentration ($C_{max}$) was reached in 0.5~8 hours, which was 324±102 ng/mL at the first administration and 328±88.0 ng/mL at the last administration. $AUC_{0-8}$ h was 1,738±415 ng·h/mL and 1,694±544 ng·h/mL, and there was no accumulation of in vivo exposure caused by the repeated administration (table 5).

TABLE 5

| Parameters | Unit | Comparative example 2, 150 mg/kg, twice a day | |
| | | First dose (Day 1) | Last dose (Day 30) |
| --- | --- | --- | --- |
| $T_{max}$ | h | 5.25 ± 3.02 | 1.94 ± 2.73 |
| $C_{max}$ | ng/mL | 324 ± 102 | 328 ± 88.0 |
| $T_{1/2,z}$ | h | NA | 3.83 ± 0.53 |
| $AUC_{0-8h}$ | ng · h/mL | 1,738 ± 415 | 1,694 ± 544 |
| $AUC_{0-24h}$ | ng · h/mL | NA | 2,656 ± 1,191 |
| $AUC_{inf}$ | ng · h/mL | NA | 2,700 ± 1,220 |

The results of administering the composition in Example 1 of the present invention in a single dose of 100 mg/kg are the same as the results as in Table 3, FIG. 1 and FIG. 2 of Experimental example 1. In particular, it was confirmed that the blood drug concentration was maintained for 20 days or longer even with a single administration.

From the above results, it was confirmed that, in the case of Comparative example 2, even when administered in two separated doses a day at a high dose, the blood drug concentration was not effectively maintained due to its rapid clearance, and thus the bioavailability was low. In addition, Comparative Example 2 was administered at a dose of 300 mg/kg/day, which corresponds to a high dose of 2,800 mg/day in humans and causes a significant frequency of gastrointestinal side effects.

As a result of the foregoing, it appears that the orally administered niclosamide formulation currently on the market has difficulty in maintaining blood drug concentration and exhibiting an effective bioavailability as described above.

On the other hand, it was confirmed that the composition of the present invention maintains an effective blood drug concentration for a long time, demonstrating effective niclosamide bioavailability.

Experimental Example 3. Efficacy Test Against SARS-CoV-2 Virus

An efficacy test for the composition of the present invention against SARS-CoV-2 virus (COVID19 virus) was performed on fifteen 24-month-old female ferrets (*Mustela putorius furo* (Virus Free Certified)). After stocking the ferrets, they were categorised by body weight (700-1,280 g) during the acclimatization phase to ensure that the body weight was evenly distributed, and the temperature (21-23° C.) and humidity (50-60%) were maintained during the test period. The ferrets were classified into a negative control group, an infection group, and a treatment group.

The negative control group consists of healthy animals that have not been infected with the virus (3 animals).

As for the infection group, only excipients were administered to virus-infected animals (6 animals).

As for the treatment group (6 animals), the niclosamide delayed-release formulation prepared in Example 1 was divided into two equal portions by taking 65 mg/kg of niclosamide, which is an active ingredient, and was intramuscularly injected into the left and right thighs of the virus-infected animals.

Specifically, 0.5 mL of $1×10^6$ $TCID_{50}$/mL SARS-CoV-2 virus was inoculated into the nasal cavity and the trachea, respectively, in total 1.0 mL. 4 hours after virus infection, the composition of Example 1 and the excipient were administered to each group.

TABLE 6

| Group | Number of animals | Administered substance | Concentration of substance (mg/mL) |
| --- | --- | --- | --- |
| Negative control group | 3 | — | — |
| Infection group | 6 | Excipient | — |
| Treatment group | 6 | Composition of Example 1 | 65 mg/kg of niclosamide |

At 3 days of post infection (3 DPI) and 6 days of post infection (6 DPI), three animals were autopsied to measure the viral titer in the lung tissue, and at 4 days of post infection (4 DPI) and 6 days of post infection (6 DPI), nasal washing sample was collected.

3-1. Viral Titer Measurement in Nasal Washing Sample

Three days after SARS-CoV-2 virus infection, viral titer was measured. The viral titer to the nasal washing sample collected after virus infection was measured using Vero cells. Specifically, 20 ul of the sample was put into 180 ul of medium comprising 5% penicillin/streptomycin (GIBCO) in a 96-well plate, and a ten-fold serial dilution ($10^0$-$10^{-7}$) was performed. The sample diluted as above was inoculated into monolayer Vero cells, and cultured for 72 hours, and then the cytopathic effect (CPE) was observed. Thereafter, the cells were stained with 1% crystal violet.

As shown in FIG. 4, upon measuring the viral titer in nasal washing sample, it was found that the treatment group had a significantly lower viral titer than the infection group after 4 and 6 days of virus infection.

3-2. Viral Titer Measurement Using qRT-PCR

The lungs were excised three days after infection with the SARS-CoV-2 virus, and the viral titer was measured. Specifically, RNA was extracted from the excised lung sample using the RNeasy Mini kit (QIAGEN, Hilden, Germany), and cDNA was obtained by performing RT-PCR. qRT (real time)-PCR was performed using the obtained cDNA as a template and using a primer for E (viral envelope) of the following table 7 as 10 ng RNA/tube. qRT-PCR was performed according to the product manual using Bio-rad SYBR Master Mix.

As a result, no virus was detected in the lung excised three days after SARS-CoV-2 viral infection, as shown in FIG. 5, and the virus infection was treated by the composition of the present invention.

TABLE 7

| Gene | Direction | Sequence (5'-3') | SEQ. ID No. |
| --- | --- | --- | --- |
| E (viral envelope) | Forward | gttgatgagcctgaagaacatgtcc | 1 |
| | Reverse | cgtacctgtctcttccgaaacg | 2 |
| GAPDH | Forward | tgcggccaaggcagtag | 3 |
| | Reverse | tgttgaagtcgcaggagac | 4 |
| CCL5 | Forward | caccggtaccatgaaggtct | 5 |
| | Reverse | gcacttgctgctggtgtaa | 6 |
| IFNr | Forward | ccatcaaggaagacatgcttgttgtc agg | 7 |
| | Reverse | gaaacacactgtgact | 8 |
| IL-6 | Forward | caaatgtgaagacagcaaggaggca | 9 |
| | Reverse | tctgaaactcctgaagaccggtagtg | 10 |

Also, the fold change of each cytokine was confirmed as a value obtained by normalizing each GAPDH after performing qRT-PCR using the primers of GAPDH, CCL5, IFN-r and IL-6 listed in Table 7 above. For statistics, one-way ANOVA or two-way ANOVA was used, One-way ANOVA (real time PCR) was used when samples were obtained for just one day, and two-way ANOVA (weight, body temperature, viral titer) was used when samples were analyzed for more than two days after infection. In addition, when performing statistical analysis using Dunnett's multiple comparisons test in two-way ANOVA, the statistics are statistical values for a comparison between the groups, and Tukey's multiple comparisons test is a value obtained by comparing and analyzing the value before infection.

In the case of virus infections, 'cytokine storm' is pointed out as one of the leading causes of death. Cytokine storm is a phenomenon in which the immune system overreacts in order to combat an invading virus in the body, attacking even normal cells. Excessive secretion of cytokines, a typical immunological material, produces secondary infectious diseases by deforming DNA in normal cells, and cytokine storms have been identified as primary causes of death in cases of Spanish flu, avian flu, and COVID-19, all of which have had high fatality rates.

As shown in FIG. 6, the composition of the present invention reduces CCL5, IFN-γ, and IL-6, which causes a cytokine storm and inflammatory cell infiltration in lung tissue. This indicates that the composition of the present invention may even suppress cytokine storm and inflammatory response caused by virus infection.

3-3. Histopathology Examination

Six days after virus infection, the lung of the treatment group was excised and a histopathology examination was performed.

Specifically, after fixing the tissue and cutting it into a certain size, the tissue went through the processes of dehydration, clearing, paraffin infiltration for 16 hours using a tissue processor (SAKURA Tissue-Tek VIP 5 Jr., JAPAN), and then a paraffin block was prepared using an embedding machine (SAKURA Tissue-Tek, JAPAN). The paraffin block was sliced to a thickness of 4 μm using a slicer (Thermo HM 340E, USA), and then the sliced fragments were attached to a slide.

The fragments attached to the slides were stained with Hematoxylin & Eosin after a deparaffin process using xylene and a dehydration process using alcohol. After staining, clearing with water, and going through dehydration using ethanol and xylene, the fragments were encapsulated, and then histopathological changes were observed using an optical microscope (Olympus BX53, Japan).

As a result, as shown in FIG. 7, when the composition of the present invention was administered to a virus-infected animal, it was confirmed that no inflammatory prognosis was found in the lung.

The above results show that the niclosamide delayed-release composition of the present invention may achieve and maintain a blood drug concentration that could not be achieved by a conventional formulation, thereby exhibiting a preventive and/or therapeutic effect on viruses. Furthermore, the composition of the present invention can reduce cytokine storm which is caused by virus infection and causes high fatality rate, and can even suppress inflammatory response. As such, the composition of the present invention can be used as a useful therapeutic agent for COVID-19, such as SARS-CoV-2 virus infection.

The foregoing description of the present invention has been presented for illustrative purposes, and it is apparent to a person having ordinary skill in the art that the present invention can be easily modified into other detailed forms without changing the technical idea or essential features of the present invention. Therefore, it should be understood that the forgoing embodiments are by way of example only, and are not intended to limit the present disclosure. For example, each component which has been described as a unitary part can be implemented as distributed parts. Likewise, each component which has been described as distributed parts can also be implemented as a combined part.

The scope of the present invention is presented by the accompanying claims, and it should be understood that all changes or modifications derived from the definitions and scopes of the claims and their equivalents fall within the scope of the present invention.

What is claimed is:

1. A method of treating coronavirus infections, comprising administering to a subject in need thereof, via an intramuscular route, a pharmaceutical composition comprising (i) niclosamide or a pharmaceutically acceptable salt thereof, (ii) sodium carboxymethylcellulose, (iii) mannitol and (iv) sodium phosphate monobasic monohydrate,
wherein the method requires maintaining a blood drug concentration of niclosamide in the subject for 20 days or longer following a single administration.

* * * * *

SEQUENCE LISTING

```
<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Forward primer for E(viral envelope)

<400> SEQUENCE: 1
gttgatgagc ctgaagaaca tgtcc                                          25

<210> SEQ ID NO 2
<211> LENGTH: 22
<212> TYPE: DNA
<213> ORGANISM: Artificial Sequence
<220> FEATURE:
<223> OTHER INFORMATION: Reverse primer for E(viral envelope)

<400> SEQUENCE: 2
cgtacctgtc tcttccgaaa cg                                            22

<210> SEQ ID NO 3
```

-continued

```
<211> LENGTH: 17
<212> TYPE: DNA
<213> ORGANISM: Artificial Sequence
<220> FEATURE:
<223> OTHER INFORMATION: Forward primer for GAPDH

<400> SEQUENCE: 3
tgcggccaag gcagtag                                                    17

<210> SEQ ID NO 4
<211> LENGTH: 19
<212> TYPE: DNA
<213> ORGANISM: Artificial Sequence
<220> FEATURE:
<223> OTHER INFORMATION: Reverse primer for GAPDH

<400> SEQUENCE: 4
tgttgaagtc gcaggagac                                                  19

<210> SEQ ID NO 5
<211> LENGTH: 20
<212> TYPE: DNA
<213> ORGANISM: Artificial Sequence
<220> FEATURE:
<223> OTHER INFORMATION: Forward primer for CCL5

<400> SEQUENCE: 5
caccggtacc atgaaggtct                                                 20

<210> SEQ ID NO 6
<211> LENGTH: 19
<212> TYPE: DNA
<213> ORGANISM: Artificial Sequence
<220> FEATURE:
<223> OTHER INFORMATION: Reverse primer for CCL5

<400> SEQUENCE: 6
gcacttgctg ctggtgtaa                                                  19

<210> SEQ ID NO 7
<211> LENGTH: 29
<212> TYPE: DNA
<213> ORGANISM: Artificial Sequence
<220> FEATURE:
<223> OTHER INFORMATION: Forward primer for IFNr

<400> SEQUENCE: 7
ccatcaagga agacatgctt gttgtcagg                                       29

<210> SEQ ID NO 8
<211> LENGTH: 16
<212> TYPE: DNA
<213> ORGANISM: Artificial Sequence
<220> FEATURE:
<223> OTHER INFORMATION: Reverse primer for IFNr

<400> SEQUENCE: 8
gaaacacact gtgact                                                     16

<210> SEQ ID NO 9
<211> LENGTH: 25
<212> TYPE: DNA
<213> ORGANISM: Artificial Sequence
<220> FEATURE:
<223> OTHER INFORMATION: Forward primer for IL-6

<400> SEQUENCE: 9
```

-continued

```
caaatgtgaa gacagcaagg aggca                                    25

<210> SEQ ID NO 10
<211> LENGTH: 26
<212> TYPE: DNA
<213> ORGANISM: Artificial Sequence
<220> FEATURE:
<223> OTHER INFORMATION: Reverse primer for IL-6

<400> SEQUENCE: 10
tctgaaactc ctgaagaccg gtagtg                                   26
```